(12) United States Patent
Owaki et al.

(10) Patent No.: US 6,953,590 B1
(45) Date of Patent: Oct. 11, 2005

(54) TAPE MATERIAL FOR TRANSCUTANEOUS ABSORPTION

(75) Inventors: Yukino Owaki, Kashima (JP); Michiyo Hashimoto, Kashima (JP); Isamu Sakamoto, Kashima (JP); Kunio Takiguchi, Kobe (JP); Yoetsu Toyoshima, Nara (JP)

(73) Assignees: Yutoku Pharmaceutical Ind. Co., Ltd., Kashima (JP); Maruho Kabushiki Kaisha, Osaka (JP)

( * ) Notice: Subject to any disclaimer, the term of this patent is extended or adjusted under 35 U.S.C. 154(b) by 0 days.

(21) Appl. No.: 09/786,370
(22) PCT Filed: Sep. 9, 1999
(86) PCT No.: PCT/JP99/04905
§ 371 (c)(1), (2), (4) Date: Mar. 15, 2001
(87) PCT Pub. No.: WO00/19986
PCT Pub. Date: Apr. 13, 2000

(30) Foreign Application Priority Data
Oct. 5, 1998 (JP) .................................. 10/282197

(51) Int. Cl.⁷ ........................ A61F 13/00; A61F 13/02; A61L 15/16
(52) U.S. Cl. ..................... 424/449; 424/400; 424/443; 424/447; 424/448; 514/818; 514/947
(58) Field of Search ................................ 424/400, 443, 424/447, 448, 449, 484, 485, 445, 486; 514/964, 514/818

(56) References Cited

U.S. PATENT DOCUMENTS

4,523,024 A * 6/1985 Shiono et al. .............. 549/407
4,963,361 A 10/1990 Kawazi (Continued)

FOREIGN PATENT DOCUMENTS

| EP | 0 285 181 | 10/1988 |
| EP | 0 331 392 | 9/1989 |
| JP | 60-204714 | 10/1985 |
| JP | 63-246327 | 10/1988 |

(Continued)

OTHER PUBLICATIONS

K. Miura, et al., The Journal of the Japan Society of Pain Clinicians, vol. 4, No. 2, "Application to Trigeminal Neuralgia of Lidocaine Tape (Trademark "Penles")", pp. 129-131, 1997 (submitting English translation only, pp. 1-8).

Primary Examiner—Gary Kunz
Assistant Examiner—Sharmila S Gollamudi
(74) Attorney, Agent, or Firm—Oblon, Spivak, McClelland, Maier & Neustadt, P.C.

(57) ABSTRACT

A preparation for transdermal absorption is disclosed which is suited for alleviating lasting pains caused by herpes zoster or postherpetic neuralgia and is practical and more improved in drug efficacy, safety and application characteristics. This tape preparation for transdermal absorption is obtained by causing an adhesive mass prepared by incorporating 1–30 parts by weight of a local anesthetic as an active ingredient in 100 parts by weight of a nonaqueous adhesive mass base comprising 5–50% by weight of a styrene-isoprene-styrene block copolymer, 1–60% by weight of an alicyclic saturated hydrocarbon resin, 5–60% by weight of liquid paraffin and 1–30% by weight of butyl rubber to be supported on a backing.

16 Claims, 3 Drawing Sheets

U.S. PATENT DOCUMENTS

| | | | |
|---|---|---|---|
| 5,827,528 A * | 10/1998 | Kubo et al. | 424/443 |
| 5,827,529 A * | 10/1998 | Ono et al. | 424/448 |
| 5,866,157 A * | 2/1999 | Higo et al. | 424/448 |
| 6,139,866 A * | 10/2000 | Chono et al. | 424/443 |
| 6,177,098 B1 * | 1/2001 | Kawaji et al. | 424/443 |

FOREIGN PATENT DOCUMENTS

| | | | |
|---|---|---|---|
| JP | 01-297059 | | 11/1989 |
| JP | 01-297069 | | 11/1989 |
| JP | 01-299215 | | 12/1989 |
| JP | 04-321624 | | 11/1992 |
| JP | 05-017346 | | 1/1993 |
| JP | 07-048250 | | 2/1995 |
| JP | 07-126157 | * | 5/1995 |
| JP | 07-215850 | | 8/1995 |
| JP | 07-233054 | | 9/1995 |
| JP | 07233054 | * | 9/1995 |
| JP | 08-319234 | | 12/1996 |
| JP | 10-095729 | | 4/1998 |
| JP | 10-147521 | * | 6/1998 |

* cited by examiner

TAPE MATERIAL FOR TRANSCUTANEOUS ABSORPTION

TECHNICAL FIELD

The present invention relates to a tape preparation for transdermal absorption suited for causing a local anesthetic to be sustainedly absorbed percutaneously and, more particularly, to a tape preparation for transdermal absorption which can cause a local anesthetic, such as lidocaine, to be absorbed through the skin stably and over a long period of time and can be used for alleviating the pain resulting from herpes zoster (hereinafter referred to HZ for short) or postherpetic neuralgia (hereinafter referred to PHN for short), for instance.

BACKGROUND ART

HZ is a disease caused by varicella-zoster virus (hereinafter referred to as VZV for short). About 95% of people experience primary infection with VZV in their childhood and acquire life-long immunity after cure. However, VZV itself, after the infection, is carried latent in sensory ganglions all over the body. While most people manifest no symptoms even after VZV having becoming latent, some people allow reactivation and propagation of VZV hidden in ganglions due to weakened responses in their immunologic mechanism and, whereby vesicles and neuralgia are manifested in the nerve field invariably unilaterally and zonally.

HZ as a result of this reactivation of VZV occurs in several parts simultaneously mainly on the chest and/or face. Eruption subsides, on an average, in about 3 weeks and neuralgia gradually abates in 1 to 3 months. And, in the aged, intractable neuralgia called PHN may remain or recur, causing troubles in everyday life, such as insomnia. The pain caused by VZV includes acute stage (HZ) pain and PHN, among which PHN, in particular, has been very difficult to treat effectively.

In cases where the pain due to HZ is slight, oral administration of an NSAID (nonsteroidal anti-inflammatory drug) is effective as the case may be, whereas, in the case of severe pain, it is necessary to perform nerve block. In the case of PHN, it is difficult to produce analgesic effects on severe pains in old cases having a history of 1 year or longer even by means of nerve block. Generally, administration of an NSAID is ineffective and, although oral administration of a tricyclic antidepressant or clonidine, iontophoresis with lidocaine, application of a 0.075% capsaicin ointment, a 2% aspirin ointment or a lidocaine ointment and use of an indomethacine patch and so forth have been attempted, there is almost no effective key therapeutic method available at present.

The local anesthetic effect of lidocaine is well known, and lidocaine has already been used in nerve block or iontophoresis as a treatment to alleviate the pain of HZ and PHN. These methods, however, require patients to receive regular outpatient treatment and often produce some problems, namely its anesthetic effect is unreliable and it causes anxiety about infection upon its injection or about electric shock. Therefore, the establishment of an effective therapeutic method has been desired which enables home treatment, gives no feeling of anxiety to patients and is free of the possibility of infection by frequent injections.

As a method for realizing such desire, a therapeutic method is conceivable which uses a medicinal means, such as an oral administration or an external administration, other than injection or dripping. Generally, however, as frequently reported for oral preparations, there are problems, for example long-term use may result in manifestation of side effects such as gastrointestinal disorder and the drug has to pass through the liver before arriving at the target site and therefore undergoes partial degradation in the liver (first pass effect). A further known drawback is that even if a side effect should have once been produced after administration, the drug can never be removed.

Therefore, various preparations suited for transdermal administration have been reported as dosage forms capable of removing these drawbacks. As external lidocaine preparations, ointments, jellies, sprays and the like have been marketed but, as far as skin surface anesthesia is concerned, satisfactory anesthetic effects have not been obtained as yet. Further, lidocaine gels as hospital preparations are sometimes used in the treatment of HZ and PHN but an ODT (occlusive dressing technique) is required after application. The development of an effective patch which can be used in a simple and easy manner has thus been desired. No such one has been marketed as yet.

Meanwhile, Japanese Patent Prepublication No. 02-300138 discloses a lidocaine-containing "composition characterized in that a long-term pain-alleviating effect is sustained after removal of the preparation". However, as can be deduced from the mere description "the effect was evaluated at one-hour intervals following lidocaine application for 4 hours", the preparation is expected only to be effective for about 4 hours at the longest. A preparation which is effective for a longer period of time is demanded.

On the other hand, Japanese Patent Prepublication No. 04-305523 discloses a patch for external use for the treatment of pain due to HZ and of PHN. This external patch is a preparation which comprises a water-soluble polymer, water and a water retaining agent as essential components and contains lidocaine or a salt thereof in the so-called aqueous poultice or cataplasm base. In this reference, moisture is said to be effective for improving the permeability of the drug. Since, in reality, however, lidocaine is scarcely soluble in water, addition of a large amount of lidocaine may result in precipitation of crystals in the water-soluble base, hence the alleged pharmacological effect is questionable. The use of a salt of lidocaine in lieu of lidocaine is also conceivable. While such a lidocaine salt itself is readily soluble in water, it is a substance hardly absorbable through the skin. The preparation disclosed in the reference cited above is thus evaluated as one that can hardly be said to be satisfactory from the viewpoint of actual drug absorption.

Further, the present inventors have already found out a patch having sustained pain-alleviating action characterized by that lidocaine as an active ingredient and an oleaginous component, as a release controlling agent, selected from the group consisting of liquid paraffins, higher fatty acids and vegetable oils are incorporated in an adhesive mass base comprising a styrene-isoprene-styrene block copolymer and a tackifier and the resulting mixture is supported on a flexible backing (Japanese Patent Prepublication No. 10-147521). The period over which the pain-alleviating effect of this preparation has been confirmed, however, is only 24 hours. A preparation capable of releasing a local anesthetic, such as lidocaine, over a longer period of time is thus demanded.

For obtaining a transdermal preparation having good application characteristics, it is a matter of course that its efficacy and safety should have been confirmed and, in addition, it should have those characteristics which are fundamental to transdermal preparations and typical of patches. Thus, for instance, it should adhere to the skin well, should not cause abrasion of the stratum corneum upon peeling thereof, and should not give pain upon peeling thereof. In particular, the pain due to the diseases in question lasts long in many cases, hence repeated administrations to the painful site or sites on the skin is anticipated; therefore, it is required that the abrasion of the stratum corneum, which is causative of skin irritation, be slight. Thus, for preparing a practical transdermal preparation, it is necessary to select the adhesion, keying, cohesion and other parameters in a manner such that they are well balanced among them. In the actual circumstances, however, it can hardly be said that a transdermal preparation having fully satisfactory characteristics has so far been provided.

Thus, under the circumstances in which it can hardly be said that a practical patch suited for alleviating lasting pains, such as the pain due to HZ or PHN, is at present available, the development of a transdermal preparation more improved in efficacy, safety and application characteristics is required.

DISCLOSURE OF INVENTION

The present inventors made investigations in an attempt to obtain a transdermal preparation which contains a local anesthetic, typically lidocaine, as an active ingredient and has high practicability.

Meanwhile, patches, which are transdermal preparations, are roughly classified into two types: poultices derived from an aqueous base comprising a water-soluble polymer, water and a water-retaining agent, among others, and tape preparations derived from an oleaginous (nonaqueous) base whose base is a elastomer selected from among styrene-isoprene-styrene block copolymers, styrene-butadiene-styrene block copolymers, polybutenes, polyisoprenes, butyl rubbers, natural rubbers and the like. As a result of preliminary investigations made by the present inventors, it was found that poultices are relatively low in adhesion and difficult to retain on the affected part for a long period of time, hence are unsuitable for achieving the object of the present invention and, further, that since they contain water, they are, in an aspect, inferior in release and transdermal absorption of the main ingredient lidocaine. It was also found that they have more problems to solve as compared with oleaginous bases; for example, since their properties (which have influences on the drug release and adhesion as well) change as a result of evaporation of water after application, they are not suited for long-period application. Furthermore, it was judged that, in the case of HZ or PHN in which the pain maybe increased by external stimulation, the stimulation resulting from cooling of the affected part is also unfavorable and, therefore, water-free, oleaginous base-derived tape preparations are rather preferred.

However, tape preparations produced by merely incorporating a local anesthetic, such as lidocaine, in an oleaginous base comprising a elastomer such as mentioned above cannot attain sustained percutaenous absorbability or sufficient adhesion. Further contrivances were needed for obtaining a practical transdermal preparation for lasting pains.

Accordingly, the present inventors made intensive investigations for obtaining a nonaqueous system-based transdermal preparation which enables to prolong and sustain the effect of a local anesthetics, such as lidocaine, can be used repeatedly for a long period of time without causing abrasion of the stratum corneum and is suited for the alleviation of HZ pains or PHN and, as a result, they found that the above object can be accomplished when a adhesive mass is prepared by incorporating liquid paraffin as a release controlling agent and butyl rubber in a adhesive mass base comprising a styrene-isoprene-styrene block copolymer and an alicyclic saturated hydrocarbon resin as a tackifier component, and a local anesthetic, such as lidocaine, is incorporated in this mass, and they have now completed the present invention.

Thus, the present invention provides a tape preparation for transdermal absorption which is characterized by that a adhesive mass prepared by incorporating 1–30 parts by weight of a local anesthetic as an active ingredient in 100 parts by weight of a nonaqueous adhesive mass base comprising 5–50% by weight of a styrene-isoprene-styrene block copolymer, 1–60% by weight of an alicyclic saturated hydrocarbon resin, 5–60% by weight of liquid paraffin and 1–30% by weight of butyl rubber is supported on a backing.

BEST MODES FOR CARRYING OUT THE INVENTION

The tape preparation for transdermal absorption of the present invention is produced by preparing a adhesive mass by incorporating a local anesthetic, liquid paraffin and butyl rubber in a nonaqueous adhesive mass base comprising a styrene-isoprene-styrene block copolymer (hereinafter sometimes referred to also as "SIS"), which is a main adhesive component, and an alicyclic saturated hydrocarbon resin, which is a tackifier component, and causing the adhesive mass to be supported on a backing in the conventional manner.

The adhesive mass base component SIS is a component essential for providing adhesion required of a patch. This SIS is already available on the market as a adhesive mass base material and, in the practice of the present invention, such commercial product can be utilized. This SIS base is incorporated preferably at an amount of 5–50%, more preferably 10–40%, relative to the adhesive mass weight. When it is less than 5%, the cohesion will become reduced, which may cause such a problem as adhesive deposit after the application. When it is in excess of 50%, the mass becomes excessively hard, which may cause insufficient adhesion.

The alicyclic saturated hydrocarbon resin included in the nonaqueous adhesive mass base components is a resin capable of providing adhesion only when combined as a tackifier component with the adhesive base. If this tackifier component is absent, no adhesion can be generated, hence the function as a tape preparation cannot be performed. As examples of the alicyclic saturated hydrocarbon resin which are specifically utilizable, there may be mentioned those available on the market such as Arkon P series and Arkon M series (both being products of Arakawa Chemical Industries). This alicyclic saturated hydrocarbon resin is incorporated preferably at an amount of 1–60%, more preferably 10–50%. When the amount of this resin is smaller than 1%, the adhesion will be lost and peeling tends to occur. When it is in excess of 60%, the adhesion is so strong that pain may be caused on the occasion of peeling off, or abrasion of the stratum corneum may occur and cause skin irritation.

Further, the liquid paraffin, as an oleaginous component, controls the release of a local anesthetic, such as lidocaine, from the adhesive mass and at the same time softens the adhesive of the adhesive mass. By incorporating this, long-lasting release of the local anesthetic is realized and the tape form preparation is provided with flexible physical properties. Therefore, without using this oleaginous component, it is impossible to obtain an elastic and flexible tape preparation effective against such diseases as HZ and PHN and capable of remaining adhesive and releasing a local anesthetic, such as lidocaine, stably for along period of time. The liquid paraffin is incorporated preferably at an amount of 5–60%, more preferably 10–40%, relative to the weight of the adhesive mass. When it is less than 5%, the long-term releasability of the local anesthetic, such as lidocaine, and the ability to morphologically follow the skin will become reduced. When it is in excess of 60%, excessive flexibility will result, the cohesion will be lost and adhesive deposit may occur after the application.

Furthermore, the butyl rubber used in the tape preparation for transdermal absorption of the present invention is used to modify the flexibility of the adhesive mass, which is insufficient when the SIS is used alone, to a favorable level and prevent the cohesion of the adhesive mass from being decreased by the liquid paraffin.

By combinational using the above liquid paraffin and butyl rubber, it is intended that the long-lasting release of the local anesthetic, such as lidocaine, from the adhesive mass and an adequate level of adhesion be secured and that the stratum corneum be prevented from being abraded. For this purpose, the butyl rubber to be used in the practice of the present invention preferably has a molecular weight of about 400,000. The butyl rubber is incorporated preferably at an amount of 1–30%, more preferably 5–15% and, by doing so, an adhesive mass having high wettability and good adhesion can be obtained.

As the active ingredient local anesthetic which can be incorporated in the thus-obtained adhesive mass, there may be mentioned lidocaine, procaine, oxyprocaine, dibucaine, tetracaine, bupivacaine, mepivacaine, propitocaine, and salts of these. Such a local anesthetic is incorporated at the adhesive mass composition preferably at an amount of 1–30% by weight (hereinafter, "%" for short), more preferably 5–20%.

In the above adhesive mass composition, a filler may be incorporated for retaining the thickness of the adhesive mass layer and/or preventing the adhesive mass from becoming excessively soft and flexible and permeating through the backing. As the filler, there maybe mentioned, for example, kaolin, titanium oxide, talc, calcium carbonate, silicate salts, silicic acid, aluminum hydrate, barium sulfate, calcium sulfate and the like.

Further, an antioxidant, such as dibutylhydroxytoluene, and/or a perfume, such as peppermint oil, and other additives generally used in ordinary tape preparations may be added, when necessary, to the adhesive mass composition of the present invention.

The tape preparation for transdermal absorption of the present invention is prepared in the form of tape preparations by preparing an adhesive mass composition by mixing and dissolving the above essential components and then causing the composition to be supported on a flexible backing, as mentioned above. An example is now shown. First, an SIS and a butyl rubber base, liquid paraffin and an alicyclic saturated hydrocarbon resin, together with a filler and/or an optional ingredient or ingredients to be added where necessary, are melted and mixed up under the heat, and a local anesthetic is added thereto, followed by mixing for sufficient dissolution.

Then, this adhesive mass is casted over a flexible backing and cooled and then, if necessary, a release liner is applied, followed by cutting to an adequate surface area, whereby a tape preparation can be prepared.

The backing to be used here is preferably a flexible film- or sheet-like material so that the tape preparation for transdermal absorption can be provided with the ability to follow the movement of the skin when it is applied as a tape preparation, for instance, to such movable site. As suitable materials, there maybe mentioned, for example, nonwoven fabrics, vinyl chloride films, knitted fabrics, cotton cloths, polyurethane films and the like. Among them, nonwoven fabrics and knitted fabrics are preferred. The thickness of the adhesive mass formed on the backing is preferably 50–500 $\mu$m, more preferably 100–300 $\mu$m.

As preferred embodiments of the thus-obtainable tape preparation for transdermal absorption of the present invention, there maybe mentioned, for example, tape preparations produced by forming, on a nonwoven fabric (backing), a 100–300 $\mu$m thick layer of an adhesive mass with a lidocaine content of 5–20%, a styrene-isoprene-styrene block copolymer content of 10–40%, a liquid paraffin (oleaginous component) content of 10–40%, a butyl rubber content of 5–15% and an alicyclic saturated hydrocarbon resin (tackifier component) content of 20–50%.

The tape preparation for transdermal absorption of the present invention as explained hereinabove is highly effective not only against such diseases as HZ and PHN but also against pains on the occasion of high frequency therapy or laser therapy, pains in the treatment of liver spots or dark red birthmarks or on the occasion of biopsy, and pains at the time of skin grafting for the treatment of thermal burns or pains in the treatment of molluscum contagiosum. In addition to the above, it will be usable also against postoperative pains and pains on the occasion of dental treatment, and so forth.

The transdermal administration of a local anesthetic utilizing the tape preparation for transdermal absorption of the present invention is made either for the purpose of alleviating pains upon venipuncture or the like or for the purpose of alleviating pains caused by HZ or PHN. However, there is a great difference between both concepts of pain alleviating.

Thus, in the former case, an instantaneous action is first of all required of the preparation and it is only required that the pain alleviating effect be produced on the occasion of such treatment as venipuncture. In the latter case, on the contrary, the maintenance of effect, namely how long pains can be alleviated, is required rather than the immediate action. For meeting such requirement, from the viewpoint not only of efficacy but also of adhesion, long-period efficacy maintenance and long-period fixation on the affected part are required in the latter case while, in the former case, only about 1 hour of maintenance of such is sufficient. The period over which the effect lasts should preferably be as long as possible and the frequency of tape preparation exchange should preferably be as low as possible. For the symptom called allodynia in which mere contacting, for instance, evokes pain, such conditions are particularly favorable to the patients concerned.

The tape preparation for transdermal absorption of the present invention is characterized by that it is excellent not only in long-lasting pain-alleviating effect but also in adhesion to and ability to morphologically follow the site of application and, furthermore, the preparation is also effective for preventing the stratum corneum from being abraded. Therefore, it can be said to be a preparation very suited for the purpose of alleviating pains caused by HZ or PHN.

Although adhesive masses can also be obtained using other substances such as natural rubbers and acrylic rubbers as main adhesive components of tape preparations for transdermal absorption, it was found, as a result of investigations concerning the releasability of local anesthetics such as lidocaine, that SISs are most preferred. However, SISs alone are insufficient to provide the adhesive masses with flexibility. In attempts to modify them by conventional techniques, a phenomenon was observed that SISs, which have a molecular weight of only about 200,000, allowed the adhesive masses to penetrate through the backing, resulting in decreases in adhesion. For preventing this phenomenon, a butyl rubber with a high molecular weight, namely a molecular weight of not less than 400,000, is incorporated to thereby improve the physical properties of the adhesive mass base.

The incorporation of this butyl rubber was further found to be effective for suppressing the decrease in adhesive mass cohesion which otherwise results from the incorporation of liquid paraffin as a release controlling agent.

On the contrary, Japanese Patent Prepublication No. 02-300138 discloses examples in which a salicylate ester, such as methyl salicylate or glycol salicylate, is used as a solvent, namely as means of dissolving lidocaine in adhesive masses. When attempts were made to use such esters in the preparation of the present invention, the esters separated from adhesive masses, causing insufficient adhesion and failing to give the form of required preparations, hence they could not be used successfully.

As mentioned above, as a result of incorporation of butyl rubber in SIS, the tape preparation for transdermal absorption of the present invention has established a balance between the flexibility of the adhesive mass and the cohesion of the adhesive mass as well as the sustained release of local anesthetics and its safety in long-period application to the skin.

The following examples, comparative examples and test examples explain the present invention but those examples are by no means limitative of the scope thereof. In the examples or comparative examples, "part(s)" means "part(s) by weight" unless otherwise specified.

EXAMPLE 1

A tape preparation for transdermal absorption was prepared according to the formulation and production method shown below.

| | |
|---|---|
| Lidocaine | 5 parts |
| Styrene-isoprene-styrene block copolymer* | 22 parts |
| Butyl rubber** | 5 parts |

-continued

| | |
|---|---|
| Alicyclic saturated hydrocarbon resin*** | 33 parts |
| Liquid paraffin | 30 parts |
| Titanium oxide | 5 parts |
| Antioxidant | 0.1 part |

*Kraton D-1107 (product of Shell Chemical)
**Exxon Butyl -065 (product of Exxon Chemical)
***Arkon P-100 (product of Arakawa Chemical Ind.)

(Production Method)

The styrene-isoprene-styrene block copolymer and the other components were melted under the heat and then lidocaine was added, followed by stirring. The mass obtained was then casted over a nonwoven fabric and allowed to cool. A polyethylene terephthalate film was applied thereto, followed by cutting to an adequate size to give a tape preparation containing 1.07 mg/cm$^2$ of lidocaine.

EXAMPLE 2

A tape preparation for transdermal absorption was prepared according to the formulation and production method shown below.

| | |
|---|---|
| Lidocaine | 10 parts |
| Styrene-isoprene-styrene block copolymer* | 25 parts |
| Butyl rubber** | 5 parts |
| Alicyclic saturated hydrocarbon resin*** | 31 parts |
| Liquid paraffin | 24 parts |
| Zinc oxide | 5 parts |
| Antioxidant | 0.1 part |

*Kraton D-1107 (product of Shell Chemical)
**Exxon Butyl -065 (product of Exxon Chemical)
***Arkon P-100 (product of Arakawa Chemical Ind.)

(Production Method)

A tape preparation containing 2.14 mg/cm$^2$ of lidocaine was obtained in the same manner as in Example 1.

EXAMPLE 3

A tape preparation for transdermal absorption was prepared according to the formulation and production method shown below.

| | |
|---|---|
| Lidocaine | 20 parts |
| Styrene-isoprene-styrene block copolymer* | 26 parts |
| Butyl rubber** | 5 parts |
| Alicyclic saturated hydrocarbon resin*** | 30 parts |
| Liquid paraffin | 14 parts |
| Titanium oxide | 5 parts |
| Antioxidant | 0.1 part |

*Kraton D-1111 (product of Shell Chemical)
**Exxon Butyl-065 (product of Exxon Chemical)
***Arkon M-100 (product of Arakawa Chemical Ind.)

(Production Method)

A tape preparation containing 4.28 mg/cm$^2$ of lidocaine was obtained in the same manner as in Example 1.

COMPARATIVE EXAMPLE 1

A tape preparation for transdermal absorption was prepared according to the formulation and production method shown below.

| | |
|---|---|
| Lidocaine | 10 parts |
| Styrene-isoprene-styrene block copolymer* | 34 parts |
| Butyl rubber** | 7 parts |
| Alicyclic saturated hydrocarbon resin*** | 42 parts |
| Zinc oxide | 7 parts |
| Antioxidant | 0.1 part |

*Kraton D-1112 (product of Shell Chemical)
**Exxon Butyl -065 (product of Exxon Chemical)
***Arkon P-90 (product of Arakawa Chemical Ind.)

(Production Method)

The styrene-isoprene-styrene block copolymer and butyl rubber and the other components were melted under the heat and then lidocaine was added, followed by stirring. The mass obtained was then casted over a nonwoven fabric and allowed to cool. A polyethylene terephthalate film was applied thereto, followed by cutting to an adequate size to give a tape preparation containing 2.14 mg/cm² of lidocaine.

COMPARATIVE EXAMPLE 2

A tape preparation for transdermal absorption was prepared according to the formulation and production method shown below.

| | |
|---|---|
| Lidocaine | 10 parts |
| Styrene-isoprene-styrene block copolymer* | 25 parts |
| Butyl rubber** | 29 parts |
| Alicyclic saturated hydrocarbon resin*** | 31 parts |
| Zinc oxide | 5 parts |
| Antioxidant | 0.1 part |

*Kraton D-1107 (product of Shell Chemical)
**Exxon Butyl -065 (product of Exxon Chemical)
***Arkon P-100 (product of Arakawa Chemical Ind.)

(Production Method)

A tape preparation containing 2.14 mg/cm² of lidocaine was obtained in the same manner as in Comparative Example 1.

COMPARATIVE EXAMPLE 3

A gel preparation was prepared according to the formulation and production method shown below.

| | |
|---|---|
| Lidocaine | 10 parts |
| Polysorbate 20 | 12 parts |
| Carbomer 940 | 0.9 part |
| Diisopropanolamine | 0.8 part |
| Propylene glycol | 76.3 parts |

A gel-like preparation was prepared by thoroughly mixing up the above components until uniformity was attained.

COMPARATIVE EXAMPLE 4

A poultice preparation was prepared according to the formulation and production method shown below.

| | |
|---|---|
| Lidocaine | 5 parts |
| D-Sorbitol | 10 parts |
| Glycerol | 20 parts |
| Propylene glycol | 10 parts |
| Sodium polyacrylate | 4 parts |
| Carboxymethylcellulose sodium | 5 parts |
| Polyacrylic acid | 3 parts |
| Methyl para-hydroxybenzoate | 0.1 part |
| Propyl para-hydroxybenzoate | 0.05 part |
| Aluminum hydroxide | 0.3 part |
| Purified water | balance |
| Total amount | 100 parts |

(Production Method)

To purified water were added D-sorbitol and polyacrylic acid, followed by mixing up. Thereto was further added a solution of lidocaine in propylene glycol, followed by mixing up. To this mixture was added a dispersion of sodium polyacrylate, carboxymethylcellulose sodium, aluminum hydroxide, methyl para-hydroxybenzoate and propyl para-hydroxybenzoate in glycerol, followed by thorough mixing to give a uniform mixture. The thus-obtained adhesive mass was casted over a nonwoven fabric, and a polyethylene terephthalate film was applied thereto, followed by cutting to an adequate size to give a poultice preparation containing 5 mg/cm² of lidocaine.

COMPARATIVE EXAMPLE 5

In an inert gas atmosphere, a flask was charged with 93 parts of octyl acrylate and 7 parts of acrylic acid, 0.1 part of benzoyl peroxide was added as a polymerization initiator, and polymerization was effected in ethyl acetate while maintaining the temperature at 60° C., to give an acrylic pressure-sensitive adhesive solution (solution A) (solid content 38.9%).

To 40 parts of the solid matter in this solution was added 60 parts of lidocaine, followed by addition of ethyl acetate to give a solution with a solid content of 35%. A polyetser release liner was coated with the above solution to a thickness after drying of 20 $\mu$m, and the coating was dried at 100° C. for 5 minutes to give a pressure sensitive adhesive layer with a lidocaine content of 60%. The thus-obtained lidocaine-containing pressure sensitive adhesive layer was overlaid with a 12-$\mu$m-thick backing made of a polyester, the assembly was allowed to stand at room temperature for 24 hours to allow the lidocaine in the pressure sensitive adhesive layer to crystallize, to give a tape form preparation.

TEST EXAMPLE 1

Applicability test:

The tape preparations and poultice preparation (cut to a size of 10 cm×7 cm) obtained in Examples 1–3 and Comparative Examples 1, 2, 4 and 5 were each applied to the lateral region of the chest (where HZ is found frequently), which is a region showing relatively great movements, of each healthy human adult. At 12 hours, 24 hours and 48 hours after application, the preparations were observed for their conditions of adhesion. The results are shown in Table 1 (n= 20).

TABLE 1

| | Number of persons (out of 20) showing the conditions of adhesion defined below | | | | | | | | |
|---|---|---|---|---|---|---|---|---|---|
| | After 12 hours | | | After 24 hours | | | After 48 hours | | |
| | No turn up | Slight turn up | Dropping | No turn up | Slight turn up | Dropping | No turn up | Slight turn up | Dropping |
| Exam. 1 | 20 | 0 | 0 | 20 | 0 | 0 | 20 | 0 | 0 |
| Exam. 2 | 20 | 0 | 0 | 20 | 0 | 0 | 20 | 0 | 0 |
| Exam. 3 | 20 | 0 | 0 | 20 | 0 | 0 | 20 | 0 | 0 |
| Comp. 1 | 0 | 10 | 10 | 0 | 5 | 15 | 0 | 0 | 20 |
| Comp. 2 | 0 | 5 | 15 | 0 | 0 | 20 | 0 | 0 | 20 |
| Comp. 4 | 0 | 10 | 10 | 0 | 3 | 17 | 0 | 0 | 20 |
| Comp. 5 | 0 | 15 | 5 | 0 | 5 | 15 | 0 | 0 | 20 |

As is obvious from Table 1, the preparations of Examples 1–3 remained satisfactorily adhering to the skin after 48 hours and scarcely showed skin irritation. The preparations of Comparative Examples 1, 2, 4 and 5 were somewhat inferior in adhesion and showed a certain extent of skin irritation.

TEST EXAMPLE 2

Pharmacokinetic test:
Intradermal pharmacokinetics of lidocaine were studied in guinea pigs.

The lateral abdominal region of each guinea pig was cut off by means of hair clippers and a shaver, cleanly wiped with water-moistened absorbent cotton and, after removal of moisture, the preparation obtained in Example 2 was administered. A protective tape was applied to the site of administration for fixation of the preparation.

(Results)

Figure 1:
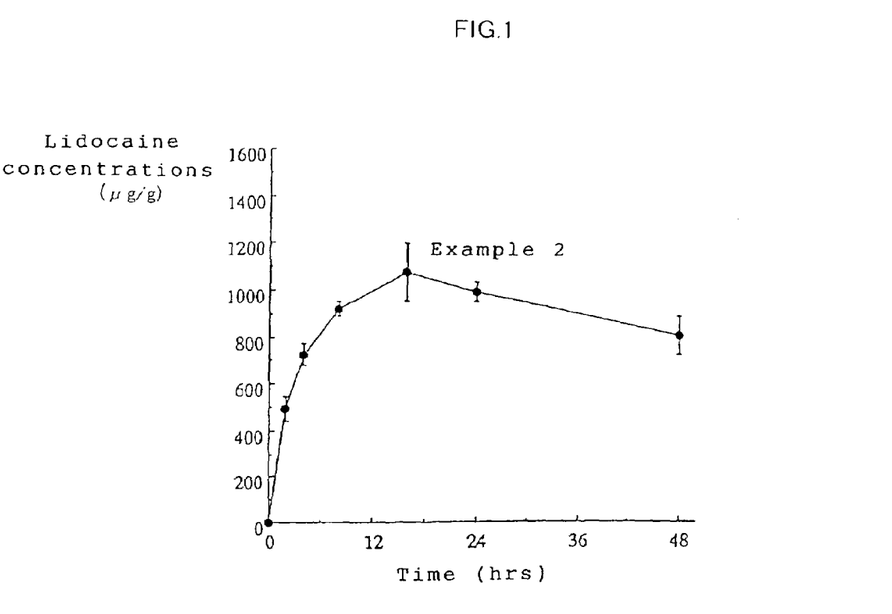
FIG. 1 shows the changes of the lidocaine concentrations in the skin following application of the preparation of Example 2.

The results of the intradermal pharmacokinetic behavior study of lidocaine are shown in FIG. 1. As is obvious from FIG. 1, the intradermal concentration of lidocaine rapidly increased after application and remained at high levels until 48 hours later.

TEST EXAMPLE 3

Local anesthetizing test in humans:
The tape preparations of Example 2 and Comparative Example 5 were tested for their anesthetic effect in humans.

The tape preparation or transdermal preparation cut to a diameter of 23 mm was applied to the inside of the upper arm of each human subject and, after peeling off, three points in the application site were pricked with a mandolin string (25 G×70 mm needle) and the level of pain was compared with that felt at an unapplied site.

(Results)

Figure 2:
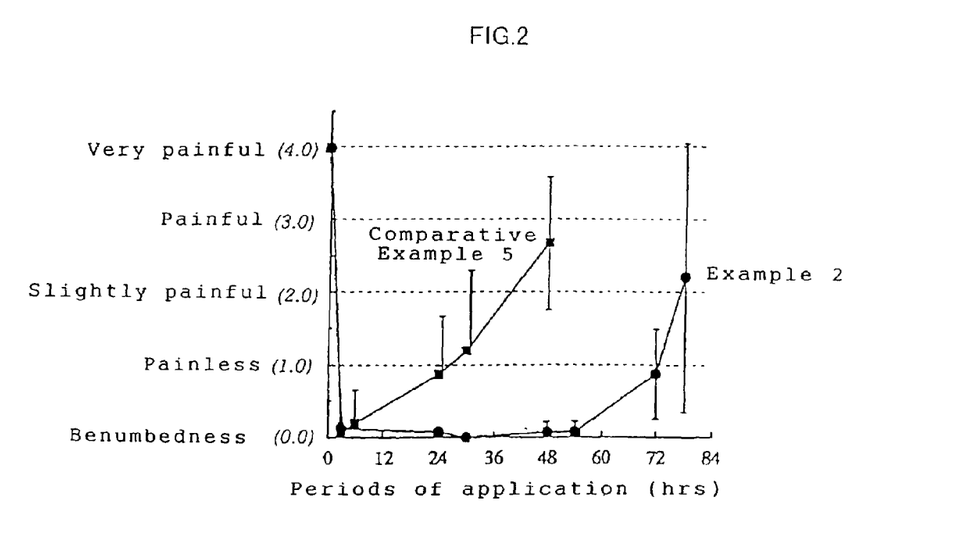
FIG. 2 shows the local anesthetic effects following application of the preparation of Example 2 and of the preparation of Comparative Example 5.

The results are shown in FIG. 2 (n=5). With the preparation of Example 2, the anesthetic effect on the level of benumbedness continued until hour 54 and the painless level, which falls within the actual therapeutic range, lasted even after hour 24 and lasted until hour 72. On the other hand, with the preparation of Comparative Example 5, the effect lasted only for at most 24 hours. This fact indicated that the long-acting tape preparation for transdermal absorption of the present invention is very useful from the viewpoint of avoiding those side effects indigenous to tape preparations, such as abrasion of the stratum corneum of the skin, sore and flare, which are anticipated if the duration of effect is short and repeated application is required.

TEST EXAMPLE 4

Measurement of the blood concentration:
For confirming the pharmacokinetics in blood after peeling off, a single application test was conducted in guinea pigs using the tape preparation of Example 2. The preparation was peeled off after 24 hours following application and the blood concentration were examined until 24 hours after peeling off. At the same time, the data were compared with those obtained in the case of application for 48 hours.

(Results)

Figure 3:
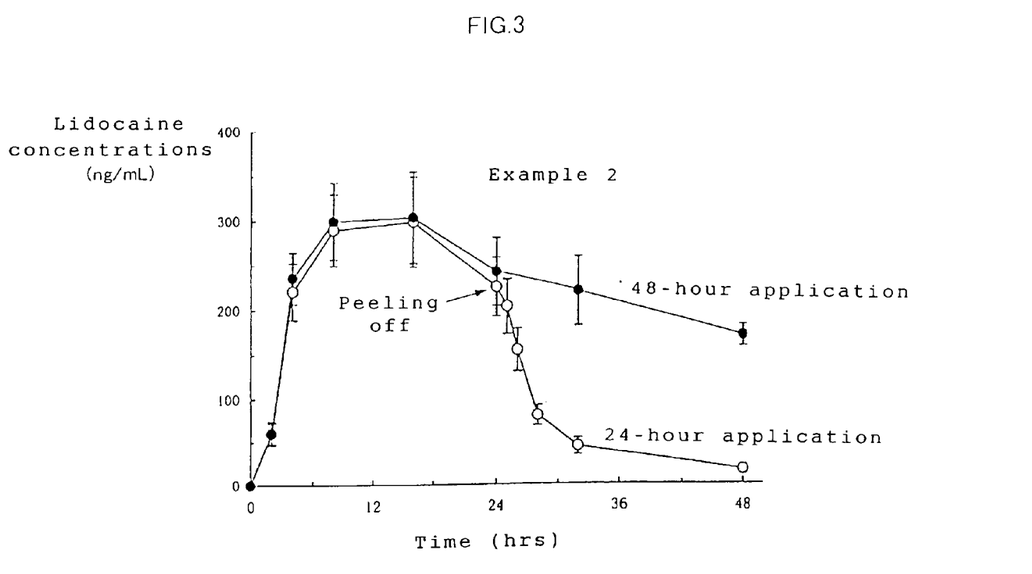
FIG. 3 shows the changes in plasma lidocaine concentrations for the case in which the preparation of Example 2 was applied for 24 hours and then peeled off and for the case in which the same preparation was continuously applied for 48 hours.

The results are shown in FIG. 3. After peeling off the preparation, the plasma concentration rapidly disappeared and it was confirmed that the plasma concentration can be maintained for 48 hours if the application is continued. This means that if a side effect should be produced, the blood concentration can be immediately and preferably reduced by peeling off the preparation, unlike injections or oral administration, as mentioned hereinabove.

TEST EXAMPLE 5

Continued application test:
Using the tape preparation of Example 2 of the present invention and the tape preparation prepared in Comparative Example 5, 4-day continuous application was conducted while making reapplication once a day at 24-hour intervals, and blood lidocaine concentration were measured. The preparation of Comparative Example was reapplied once or twice a day and, in the group receiving two reapplications per day, reapplication was performed after 10 hours and 24 hours following the preceding application. The reapplication was made at the same site for 4 days.

(Results)

Figure 4:
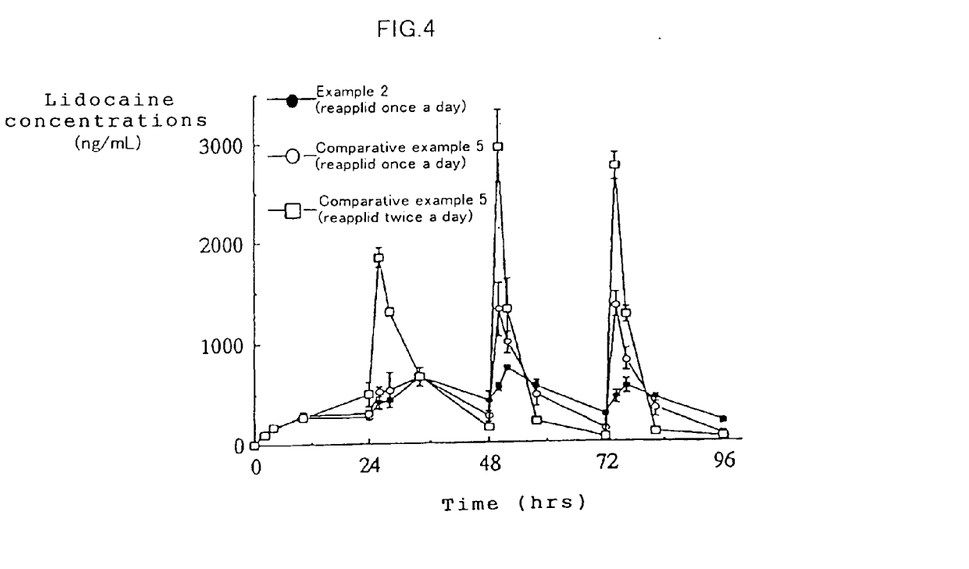
FIG. 4 shows the changes in plasma lidocaine concentrations as found when the preparation of Example 2 or Comparative Example 5 was continuously applied.

The results are shown in FIG. 4. In the continuous application test, the difference in pharmacokinetics as resulting from reapplication of the tape preparations was confirmed. While the blood lidocaine concentration rapidly increased after reapplication of the preparation of Comparative Example 5, an almost constant blood concentration was maintained with the preparation of Example 2. Since the skin stratum corneum is involved in the transdermal absorbability of lidocaine, there is the possibility of a rapid increase in blood concentration when such a preparation is applied to the skin whose stratum corneum shows reduced barrier functions due to repeated application, for instance, hence there is a safety problem. In this respect, it was shown that the influence of the preparation of Example 2 on the stratum corneum is more limited than that of the preparation of Comparative Example 5 and it was thus found that the preparation of the present invention is superior in safety.

TEST EXAMPLE 6

Stratum corneum abrasion test:

The tape preparation of Example 2 of the present invention and the tape preparation prepared in Comparative Example 5 were examined for the ability to abrade the stratum corneum. Thus, each tape preparation was applied to the upper arm of each respective normal healthy subject and peeled it off 3 hours after the application.

Each preparation removed was transcribed onto a measurement tape and, after washing with ethanol for defatting, the stratum corneum was stained with a staining solution, followed by immersion in an aqueous solution of sodium dodecyl sulfate.

The amount of the eluted staining substance was measured based on the absorbance data. Since the absorbance is proportional to the amount of stratum corneum adhering to the preparation removed, the absorbance was regarded as the amount of stratum corneum abraded.

(Results)

Figure 5:
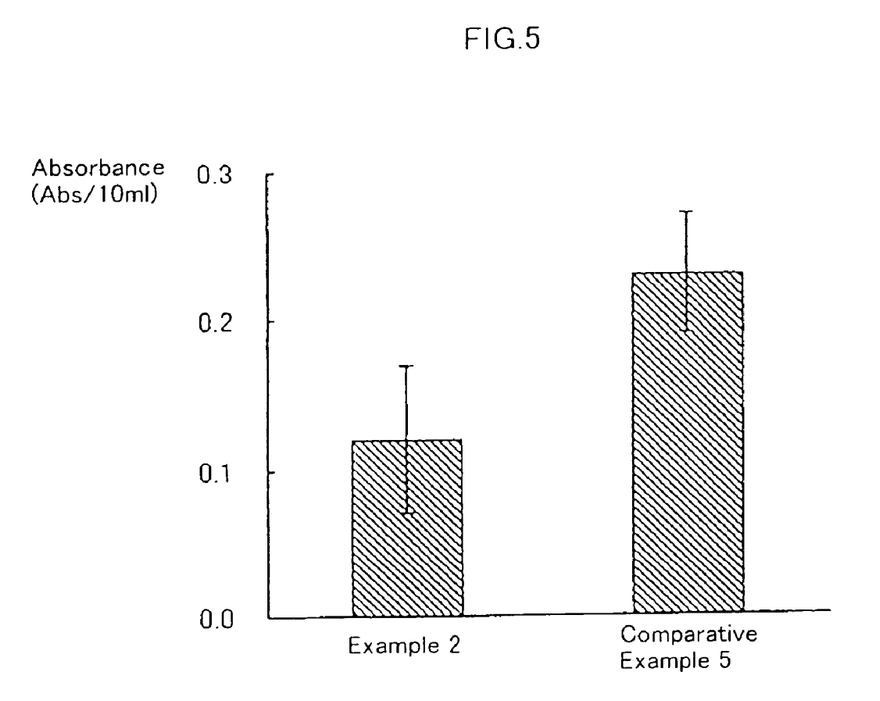
FIG. 5 shows the amounts of the stratum corneum peeled off upon peeling off the preparation of Example 2 or Comparative Example 5 following application thereof.

The results are shown in FIG. 5. As is evident from this figure, it was found that the amount of abraded stratum corneum with the tape preparation of Example 2 was smaller than that of the tape preparation of Comparative Example 5. Thus, it was shown that the tape preparation of the present invention is less in the ability to cause stratum corneum abrasion, which is causative of skin irritation, hence is superior in skin safety.

COMPARATIVE EXAMPLE 7

Clinical trial against HZ and PHN:

The tape preparation for transdermal absorption of the present invention in which lidocaine was used as the local anesthetic was applied to 11 patients complaining of pain due to HZ or PHN twice a day (one sheet per application) for 3–7 days and the pain-alleviating effect was examined.

(Results)

The results are shown below in Table 2. It was revealed that the tape preparation for transdermal absorption of the present invention is a drug useful for alleviating pains in peripheral neuralgia.

TABLE 2

| Efficacy | Global rating of improvement | |
|---|---|---|
| | Number of subjects | Percentage (%) |
| Excellent | 3 | 27.3 |
| Good | 6 | 54.5 |
| Fair | 1 | 9.1 |
| Poor | 1 | 9.1 |
| Total | 11 | 100 |
| Excellent + good | 9 | 81.8 |

TEST EXAMPLE 8

Pain-alleviating test on the occasion of high frequency therapy:

A pain alleviating test was performed using 5 patients treated for liver spot removal as panelists.

Thus, the tape preparation for transdermal absorption of the present invention in which lidocaine was used as the local anesthetic was applied to the treatment site of each patient 1 hour before liver spot removal by means of a high frequency therapy. Just before treatment, the tape preparation was peeled off and liver spot removal was effected by means of a high frequency therapy. The liver spots could be treated without any pain felt by the patient.

INDUSTRIAL APPLICABILITY

The tape preparation for transdermal absorption of the present invention can quantitatively and efficiently release lidocaine and therefore is excellent in duration of effect. It causes stratum corneum abrasion only to be a lesser extent, hence does not decrease the barrier function of the stratum corneum upon continuous application. Therefore, it is a preparation very suited for the purpose of pain alleviation in HZ or PHN and high in safety.

In addition to the above objects, it has a good pain alleviating effect against pains resulting from high frequency therapy or laser therapy, pains upon treatment of liver spots or dark red birthmarks, pains on the occasion of biopsy, and pains upon skin grafting for the treatment of thermal burns or of molluscum contagiosum, hence has high utility value.

What is claimed is:

1. A non-aqueous tape preparation comprising a nonaqueous adhesive mass consisting essentially of 1–30 parts by weight of a local anesthetic in a base form in 100 parts by weight of the nonaqueous adhesive mass base, 5–50% by weight of a styrene-isoprene-styrene block copolymer, 1–60% by weight of an alicyclic saturated hydrocarbon resin, 5–60% by weight of liquid paraffin and 1–30% by weight of butyl rubber, wherein the adhesive mass is supported on a backing, and wherein the local anesthetic is at least one selected from the group consisting of lidocaine, procaine, oxyprocaine, dibucaine, bupivacaine, mepivacaine, and propitocaine.

2. A tape preparation as claimed in claim 1, wherein the effect of the local anesthetic lasts for 24 to 72 hours.

3. A tape preparation as claimed in claim 1 which causes stratum corneum abrasion only to a slight extent even when applied continuously for a long period of time.

4. A tape preparation as claimed in claim 1 which is excellent in duration of effect on alleviating pains due to herpes zoster or postherpetic neuralgia.

5. A tape preparation as claimed in claim 1 which is excellent in duration of effect on alleviating pains on the occasion of high frequency therapy or laser therapy, pains upon treatment of liver spots or dark red birthmarks, pains upon biopsy, pains on the occasion of skin grafting for the treatment of thermal burns, or pains on the occasion of treatment of molluscum contagiosum.

6. A tape preparation as claimed in claim 1, wherein the local anesthetic is lidocaine.

7. A tape preparation as claimed in claim 1 which causes stratum corneum abrasion only to a slight extent even when applied continuously for a long period of time, and is excellent in duration of effect on alleviating pains due to herpes zoster or postherpetic neuralgia.

8. The preparation of claim 1, wherein the alicyclic saturated hydrocarbon is present in an amount of from 10–50% by weight.

9. The preparation of claim 1, wherein the styrene-isoprene-styrene block copolymer is present in an amount of from 10–40% by weight.

10. The preparation of claim 1, wherein the liquid paraffin is present in an amount of 10–40% by weight.

11. The preparation of claim 1, wherein the butyl rubber is present in an amount of from 5–15% by weight.

12. The preparation of claim 1, wherein the butyl rubber has a molecular weight of not less than 400,000.

13. The preparation of claim 1, wherein the local anesthetic in a base form is present in an amount of from 5–20% by weight.

14. The composition of claim 1 further consisting essentially of a filler, an antioxidant or a mixture thereof.

15. The preparation of claim 1, wherein the backing has a thickness of from 50–500 $\mu$m.

16. The preparation of claim 1, wherein the adhesive mass consists essentially of five parts of lidocaine, 22 parts of the styrene-isoprene-styrene block copolymer, five parts of the butyl rubber, 33 parts of the alicyclic saturated hydrocarbon resin, 30 parts of the liquid paraffin, 5 parts of titanium oxide, and 0.1 parts of an antioxidant.

* * * * *